(12) United States Patent  
Karch

(10) Patent No.: US 8,218,728 B2
(45) Date of Patent: Jul. 10, 2012

(54) COMPUTED TOMOGRAPHY SCANNER, IN PARTICULAR FOR PERFORMING A SPIRAL SCAN, AND A METHOD FOR CONTROLLING A COMPUTED TOMOGRAPHY SCANNER

(75) Inventor: Thomas Karch, Bamberg (DE)

(73) Assignee: Siemens Aktiengesellschaft, Munich (DE)

( * ) Notice: Subject to any disclaimer, the term of this patent is extended or adjusted under 35 U.S.C. 154(b) by 272 days.

(21) Appl. No.: 12/591,141

(22) Filed: Nov. 10, 2009

(65) Prior Publication Data

US 2010/0119035 A1    May 13, 2010

(30) Foreign Application Priority Data

Nov. 12, 2008  (DE) .......................... 10 2008 056 891

(51) Int. Cl.
*H05G 1/64* (2006.01)
*G21K 3/00* (2006.01)

(52) U.S. Cl. ........ 378/98.11; 378/5; 378/98.9; 378/156; 378/158

(58) Field of Classification Search ................ 378/5, 16, 378/98.9, 98.11, 156, 157, 158, 159
See application file for complete search history.

(56) References Cited

U.S. PATENT DOCUMENTS

| | | | | |
|---|---|---|---|---|
| 5,570,403 A * | 10/1996 | Yamazaki et al. | ................. | 378/5 |
| 5,661,774 A * | 8/1997 | Gordon et al. | ................. | 378/101 |
| 6,094,474 A * | 7/2000 | Vezina | ........................... | 378/156 |
| 6,148,062 A * | 11/2000 | Romeas | ........................ | 378/156 |
| 6,252,932 B1 * | 6/2001 | Arakawa | ...................... | 378/98.9 |
| 6,633,627 B2 * | 10/2003 | Horiuchi | ....................... | 378/156 |
| 6,650,730 B2 * | 11/2003 | Bogatu et al. | ................. | 378/158 |
| 6,735,273 B2 * | 5/2004 | Flohr et al. | ........................ | 378/5 |
| 6,990,171 B2 * | 1/2006 | Toth et al. | ....................... | 378/16 |
| 7,120,222 B2 * | 10/2006 | Hoffman | ........................... | 378/5 |
| 7,200,204 B2 * | 4/2007 | Distler et al. | .................. | 378/156 |
| 7,330,535 B2 * | 2/2008 | Arenson et al. | ............... | 378/158 |
| 7,474,736 B2 * | 1/2009 | Munro et al. | ................. | 378/159 |
| 7,636,413 B2 * | 12/2009 | Toth | ................ | 378/4 |
| 2005/0220265 A1 | 10/2005 | Besson | | |
| 2008/0198963 A1 | 8/2008 | Spahn | | |

FOREIGN PATENT DOCUMENTS

DE    102004031168 A1    12/2005
DE    102007044549 A1    4/2009

* cited by examiner

*Primary Examiner* — Allen C. Ho
(74) *Attorney, Agent, or Firm* — Harness, Dickey & Pierce, P.L.C.

(57) ABSTRACT

A computed tomography scanner is disclosed for performing a spiral scan. In at least one embodiment, the computed tomography scanner includes a rotatable X-ray emitter for generating a beam fan and an X-ray detector, positioned diametrically opposite to the emitter, and an associated evaluation unit. In at least one embodiment, provision is made for an X-ray filter arranged downstream of the X-ray emitter, the position of the X-ray filter being correlated to that of the X-ray detector. Further, the X-ray filter is partly inserted into the beam fan only during operation for generating an unfiltered and, simultaneously, a filtered radiation component of the beam fan, wherein the radiation components have different X-ray spectra and wherein the evaluation unit is designed for separate evaluation of a measurement signal of the unfiltered radiation component and a measurement signal of the filtered radiation component, to obtain dual-energy images.

13 Claims, 4 Drawing Sheets

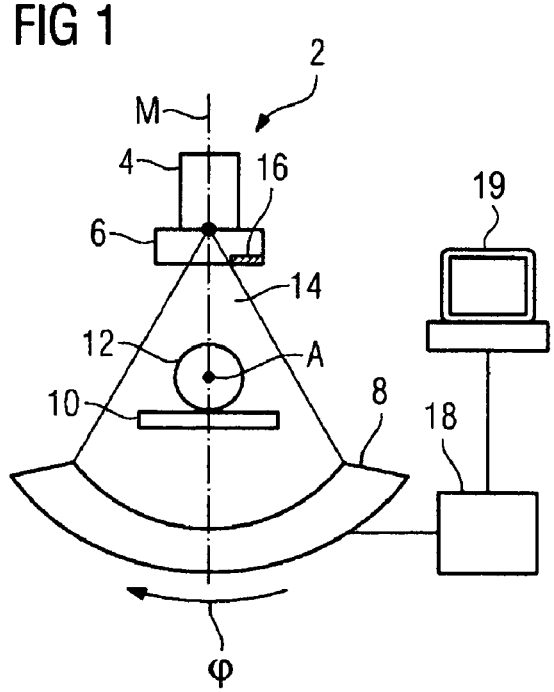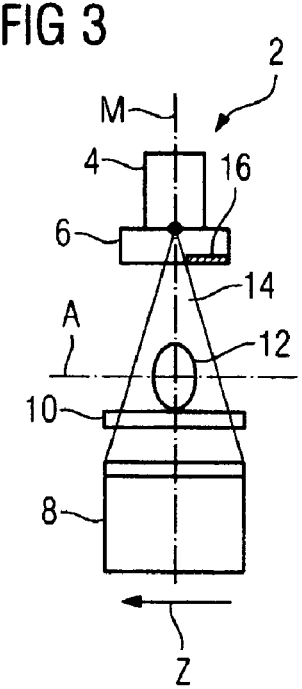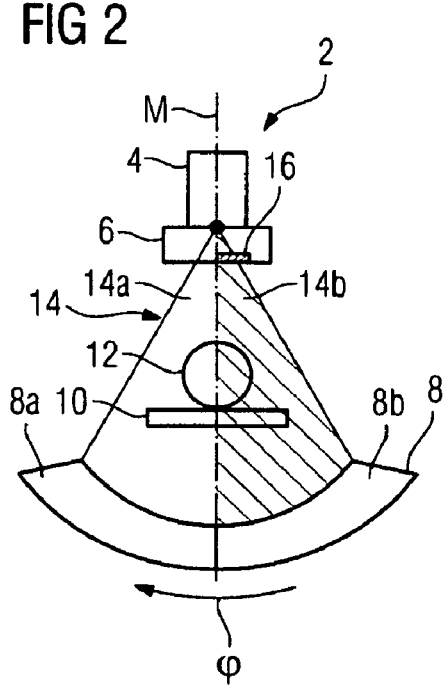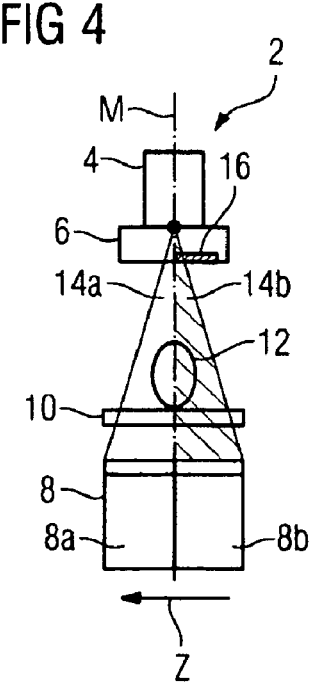

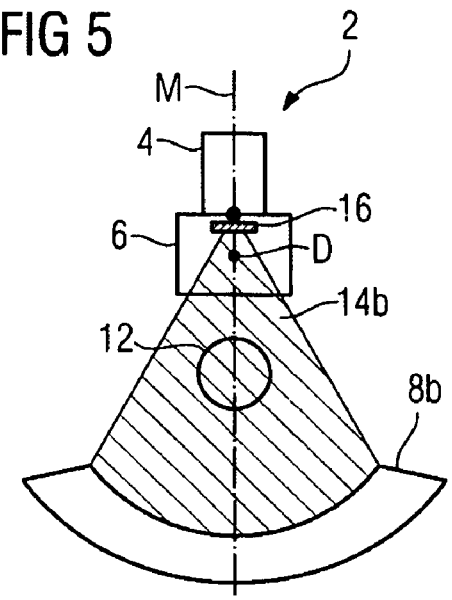
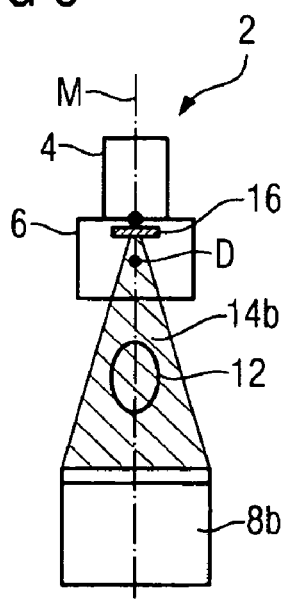
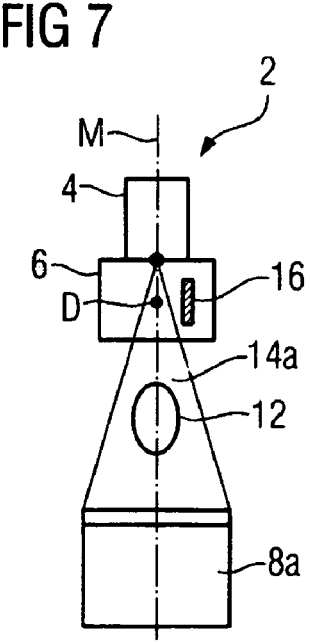

COMPUTED TOMOGRAPHY SCANNER, IN PARTICULAR FOR PERFORMING A SPIRAL SCAN, AND A METHOD FOR CONTROLLING A COMPUTED TOMOGRAPHY SCANNER

PRIORITY STATEMENT

The present application hereby claims priority under 35 U.S.C. §119 on German patent application number DE 10 2008 056 891.0 filed Nov. 12, 2008, the entire contents of which are hereby incorporated herein by reference.

FIELD

At least one embodiment of the invention generally relates to a computed tomography scanner, in particular for performing a spiral scan. At least one embodiment of the invention also generally relates to a method for controlling a computed tomography scanner.

BACKGROUND

In clinical application, the computed tomography scanner is used to acquire a data record for an X-ray image, on the basis of which a specific material is determined within an object to be examined or a patient. The aspect of material determination is becoming ever more important in routine clinical problems and so the importance and field of application of computed tomography scanners has greatly increased.

A computed tomography scanner used to recognize material during the evaluation and display of X-ray data operates on the principle of the so-called dual-energy method. In this method, the object to be examined or the patient is for example scanned with X-ray quanta up to 80 keV and X-ray quanta up to 140 keV. Here, it is possible to either use two X-ray emitters with different energies or switch the tube voltage of an X-ray emitter alternately. As a result of the different X-ray spectra of the two X-ray radiations, a differing average attenuation is generated and so more comprehensive information is gathered compared to a conventional computed tomography scanner in normal operation.

DE 10 2004 031 168 A1 describes an imaging X-ray scanner in which a two-part filter is inserted into a fan-beam-shaped beam path. The two parts of the filter arranged next to each other in the radiation direction divide the fan beam into two beam fans which differ in respect of the intensity thereof.

U.S. Pat Nos. 7,463,715 and 7,116,749 systems for dual-energy visualization, in which a rotating X-ray filter is positioned in the X-ray beam and so the spectrum of the X-ray radiation changes as a result of the rotation of the X-ray filter. Here, images are recorded alternately for each position, with each image corresponding to a different X-ray spectrum.

SUMMARY

In at least one embodiment of the invention, cost-effective and simple acquisition of dual-energy images of an object or a patient is permitted, using a single X-ray emitter.

According to at least one embodiment of the invention, a computed tomography scanner is used, in particular for performing a spiral scan, comprising a rotatable X-ray emitter for generating a beam fan and an X-ray detector, positioned diametrically opposite to said emitter, with an associated evaluation unit, wherein provision is made for an X-ray filter arranged downstream of the X-ray emitter, the position of which X-ray filter is correlated to that of the X-ray detector and said X-ray filter is partly inserted into the beam fan during operation for generating an unfiltered and, simultaneously, a filtered radiation component of the beam fan, wherein the radiation components have different X-ray spectra and wherein the evaluation unit is designed for separate evaluation of a measurement signal of the unfiltered radiation component and a measurement signal of the filtered radiation component for obtaining dual-energy images.

At least one embodiment of the invention is based on the idea that, with the aid of the X-ray filter, the X-ray radiation of a single X-ray emitter can be subdivided in respect of its X-ray spectrum. Here, the proposed X-ray filter constitutes a material-saving and simple embodiment that is distinguished by a particularly cost-effective implementation.

Here, X-ray radiation is understood to be radiation created as a result of a tube voltage applied between an anode and a cathode in the X-ray emitter and emitted by the X-ray emitter in the style of a beam fan. This X-ray radiation has a spectrum, the maximum of which in keV corresponds to the maximum of the tube voltage in kV. As it were, the use of the X-ray filter provides two spatially adjacent partial beam fans, namely the unfiltered and the filtered radiation component, which have different X-ray spectra and which penetrate the patient simultaneously and which are subsequently detected by the X-ray detector. The two radiation components are generated by the positioning of the X-ray filter which does not cover the entire beam fan. Here, the unfiltered radiation component is original X-ray radiation determined by the tube voltage.

The radiation component passing through the X-ray filter includes filtered X-ray radiation, the X-ray spectrum of which has been changed with respect to the unfiltered X-ray radiation. The change in the X-ray spectrum depends on the design of the X-ray filter, in particular on the material used and on the thickness of the filter material through which the X-ray radiation has to pass. Since the position of the X-ray filter is correlated to that of the X-ray detector, the image data recorded by the X-ray detector can be assigned to the two partial beam fans. As a result of this assignment, a scan using one X-ray emitter provides two data records containing specific information which in particular is used to determine the irradiated tissue or material.

A significant advantage of using such an X-ray filter is that the X-ray emitter for generating the two radiation components does not have to be switched but is always operated using the same tube voltage during an examination of the patient. Moreover, the proposed solution for obtaining dual-energy images is particularly cost-effective because doubled up components of the computed tomography scanner, such as two X-ray emitters operated at different tube voltages or two X-ray detectors, are not required. Moreover, the X-ray filter can be used to retrofit conventional computed tomography scanners by merely placing it in the beam fan between the X-ray emitter and the patient and by taking its position into account when evaluating the image data. The proposed acquisition of dual-energy images by filtering the X-ray radiation converts a single source computed tomography scanner into a dual energy scanner in a technically simple fashion and makes it possible to widely establish dual-energy images in clinical routine.

In respect of evaluating the data obtained by the X-ray detector in a particularly precise fashion, the position of the X-ray emitter is preferably correlated to that of the X-ray detector such that during the evaluation there is an assignment of the regions on which the X-ray detector the two radiation components are incident. If the position of the X-ray filter changes with respect to the X-ray emitter, the size and position of the portion shadowed by the X-ray filter also change. However, the size and arrangement of the portions of the X-ray detector are known at all times due to the correlation with the position of the X-ray filter and are used for real-time evaluation.

In accordance with an example embodiment variant, the X-ray filter for filtering out low-energy X-ray radiation is alternatively made of tin, aluminum, copper, titanium or tungsten. In this case, low-energy X-ray radiation is in particular understood to be the X-ray spectrum up to the maximum intensity of the emitted, unfiltered bremsstrahlung. In the process, the X-ray radiation is hardened, i.e. overall the X-ray radiation is attenuated; this attenuation affects the low-energy component more strongly and this produces a larger component of higher energy X-ray radiation in the distribution of the X-ray spectrum.

Alternatively, or additionally, it is possible to set the desired properties of the X-ray filter by selecting a suitable thickness for the filter material. Moreover, the X-ray filter can also be of two- or multi-layered design, i.e. it comprises two or more layers with differing composition which form a filter unit by being placed above one another in the radiation direction and so they are penetrated successively. A change in the X-ray spectrum is effected depending on the design of the X-ray filter (material, thickness, etc.), wherein this change is crucial compared to the unfiltered radiation component.

According to an example refinement, the X-ray filter covers a predetermined portion of the X-ray detector in a defined direction of extent of the X-ray detector. In this case, the direction of extent can be the $\phi$-direction of the X-ray detector, i.e. the longitudinal direction of the X-ray detector. Alternatively, the X-ray filter can cover a portion of the X-ray detector in the Z-direction, i.e. in the transverse direction of the X-ray detector. In both cases, the predetermined portion is known and so the measurement signals can unambiguously be assigned to the filtered and the unfiltered X-ray radiation during the evaluation. The precise calibration of the X-ray filter in the beam path can be effected by already established calibration mechanisms.

According to a further example refinement, the X-ray filter covers half of the X-ray detector in the defined direction of extent. In this refinement, the two portions of the X-ray detector, onto which the filtered and unfiltered X-ray radiation impinges, have the same size and so an area of the X-ray detector which is as large as possible is provided for both radiation components so that a sufficient measurement signal is obtained and a good image quality is attained.

The X-ray filter is advantageously displaceably arranged in the beam fan. By inserting the X-ray filter into the beam path or completely removing it from the beam path, the computed tomography system can be switched between a dual-energy and a standard mode. Moreover, as a result of the displaceable X-ray filter, an X-ray filter, the position of which can be adjusted and which is dynamic with respect to the X-ray emitter is present, and so the size of the radiation components can likewise be set as a function of the scan requirements.

Provision is made preferably for a number of X-ray filters which can be displaced into the beam fan. A number of filters which differ in respect of their material and/or their thickness are provided for the different requirements or applications. In particular, the set of X-ray filters is arranged on a common support and one or more of the X-ray filters are inserted into the beam fan depending on the filter requirements.

In accordance with one advantageous embodiment of the computed tomography scanner, the X-ray filter is displaceably arranged such that during a complete rotation of the X-ray emitter it can be adjusted at least between a cover position in which it completely covers the beam fan and a removed position in which it completely uncovers the beam fan. Hence, the motion sequence of the X-ray filter is synchronized with the rotation of the X-ray emitter. Using a simple motion mechanism, the X-ray filter can be removed from and reinserted into the beam fan in a linear fashion or during a rotation. For the evaluation this means that, during the transition from the cover position into the removed position, the portion for detecting the filtered radiation becomes ever smaller until the X-ray detector only receives the unfiltered radiation when the X-ray filter is in the removed position. Subsequently, during the displacement of the X-ray filter from the removed position into the cover position, the radiation component of the filtered radiation increases until the X-ray filter has once again assumed the cover position and the X-ray detector only receives filtered X-ray radiation.

This process can also be repeated a number of times at predetermined intervals during one rotation of the X-ray emitter around the patient. Here, the position of the X-ray filter with respect to the X-ray detector is known at all times and so the evaluation of the two measurement signals is not falsified. This method obtains a pulsing of the unfiltered and filtered X-ray radiation.

In respect of a particularly efficient embodiment of a displaceable X-ray filter, the X-ray filter is preferably arranged in rotatable fashion. In particular, the X-ray filter rotates about a central axis of the beam fan. When, during its rotation, the X-ray filter is perpendicular to the central axis, it covers the entire beam fan. Alternatively, when the X-ray filter extends parallel to the central axis of the beam fan and is completely outside of the beam fan, the X-ray detector only detects the unfiltered radiation. In the other positions the X-ray filter covers an ever increasing or decreasing portion of the X-ray detector during the rotation of said filter and so both the filtered and unfiltered X-ray radiation is measured.

In respect of a refinement with a particularly simple design, the X-ray emitter preferably comprises an emitter diaphragm, the X-ray filter being installed in the latter. Conventional computed tomography scanners are generally provided with an emitter diaphragm which forms the beam fan. Here, enhancing the diaphragm with an X-ray filter can be implemented in a fairly simple technical fashion. The emitter diaphragm can be replaced in a simple fashion, as a result of which even existing standard computed tomography scanners can be retrofitted for dual-energy imaging.

Preferably, the computed tomography scanner can be operated in normal operation without an X-ray filter and in a dual-energy mode with an X-ray filter, wherein a feed velocity of a patient couch relative to the X-ray emitter is reduced in the dual-energy mode in the case of a spiral scan. Since the use of the X-ray filter means that only a portion of the X-ray detector is available for each of the two radiation components, a lower couch feed is required in order to generate a complete image data record for each radiation component. For example, if the X-ray filter covers half of the X-ray detector during the spiral scan, twice as many rotations of the X-ray emitter around the patient are required in order to obtain the same amount of information for both the filtered and the unfiltered X-ray radiation as during operation without the X-ray filter.

Furthermore, according to an embodiment of the invention, a method is disclosed for controlling a computed tomography scanner, in particular for performing a spiral scan, wherein the computed tomography scanner comprises an X-ray emitter for generating a beam fan and an X-ray detector, positioned diametrically opposite to said emitter, with an associated evaluation unit, wherein a rotatable X-ray filter is arranged downstream of the X-ray emitter, the position of which X-ray filter is correlated to that of the X-ray detector, an unfiltered and, simultaneously, a filtered radiation component of the beam fan is formed using the X-ray filter which is only partly inserted into the beam fan (14), wherein the radiation components have different X-ray spectra, and a measurement signal of the unfiltered radiation component is evaluated separately from a measurement signal of the filtered radiation component for obtaining dual-energy images.

The advantages and example embodiments listed in respect of the computed tomography scanner should be transferred in analogous fashion to the method for controlling the computed tomography scanner.

BRIEF DESCRIPTION OF THE DRAWINGS

The invention will be described in more detail on the basis of the example embodiments illustrated in the drawings, in which, in a schematic and much simplified form, FIG. 1 shows a front view of a computed tomography scanner during normal operation, FIG. 2 shows a front view of the computed tomography scanner in accordance with FIG. 1 during dual-energy operation, FIG. 3 shows a side view of a computed tomography scanner during normal operation, FIG. 4 shows a side view of the computed tomography scanner in accordance with FIG. 3 during dual-energy operation, FIG. 5 shows a front view of a computed tomography scanner with a rotating X-ray filter which completely covers a beam fan, FIGS. 6-11 show side views of the computed tomography scanner in accordance with FIG. 5, wherein the X-ray filter is in different positions during its rotation.

Figure 8:
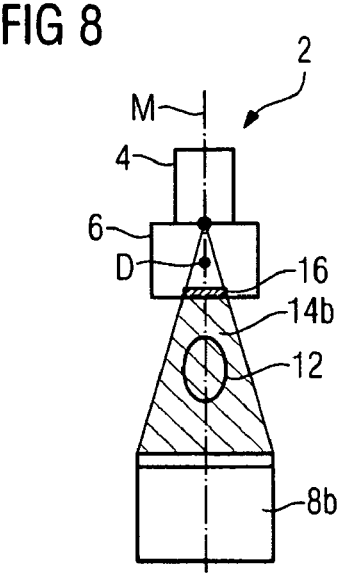

In the figures, parts having the same effect are provided with the same reference signs.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 schematically illustrates a computed tomography scanner 2 which in the illustrated example embodiment is specified by an X-ray emitter 4, an emitter diaphragm 6 arranged downstream of the X-ray emitter 4 and an X-ray detector 8 positioned diametrically opposite to the X-ray emitter 4. The X-ray emitter 4 and the X-ray detector 8 are arranged rotatably about an axis A running perpendicular to the plane of the drawing. A patient couch 10 extends along the axis A and so, during operation, the components of the computed tomography scanner 2 rotate about a patient 12 supported by the patient couch 10. The rotation of the computed tomography scanner 2 is combined with a feed of the patient couch 10 along the axis A, as a result of which there is a spiral scan of the patient 12.

In this case, the X-ray emitter 4 comprises a cathode and an anode (neither illustrated in any more detail) arranged in a vacuum housing. An adjustable tube voltage of approximately 25 kV to approximately 150 kV is applied between the cathode and the anode. As a result of this tube voltage, electrons emitted by the cathode are accelerated toward the anode and said electrons impinge on the latter with an energy of at most 25 keV to 150 keV. X-ray radiation is generated as the electrons impact, it leaves the vacuum housing through a beam output window and it is shaped about a central axis M by the emitter diaphragm 6 in the manner of a beam fan 14. The X-ray radiation has an energy distribution, the maximum energy of which in kiloelectronvolts numerically equals the tube voltage in kilovolts applied between the cathode and the anode. In the case of a tube voltage of e.g. 140 kV, the maximum X-ray radiation therefore has an energy of 140 keV. Most of the X-ray radiation however has an energy in the range of approximately half to ⅔ of the tube voltage.

An X-ray filter 16 which can be displaced linearly into the beam fan 14 is installed in the emitter diaphragm 6, as becomes apparent from FIG. 2. The beam fan 14 is incident on the two-dimensional X-ray detector 8 which has an arced design for detecting all the X-ray radiation and which extends in a φ-direction coinciding with the longitudinal direction of the X-ray detector 8 and a Z-direction specifying the transverse direction of the X-ray detector 8. In the example embodiment illustrated in FIG. 1 and FIG. 2, the X-ray filter 16 can be displaced in the φ-direction of the X-ray detector 8.

When the X-ray filter 16 is inserted into the beam fan 14, two radiation components 14a, 14b are created, the energy distributions of which are in two different energy ranges. The radiation component 14a is unfiltered and has the energy distribution at which the X-ray emitter 14 is operated. The filtered radiation component 14b, illustrated by a shaded surface, passes through the X-ray filter 16 and so its X-ray spectrum is limited compared to the unfiltered X-ray radiation 14a.

By way of example, a tube voltage of 140 kV is applied between the cathode and the anode. The X-ray filter 16 is made of a metal such as e.g. tin which attenuates the low-energy component of the X-ray radiation more strongly than the high-energy component. The unfiltered X-ray radiation 14a impinges on a portion 8a of the X-ray detector 8. At the same time, the remaining portion 8b of the X-ray detector 8 measures a signal of the filtered X-ray radiation 14b.

Figure 12:
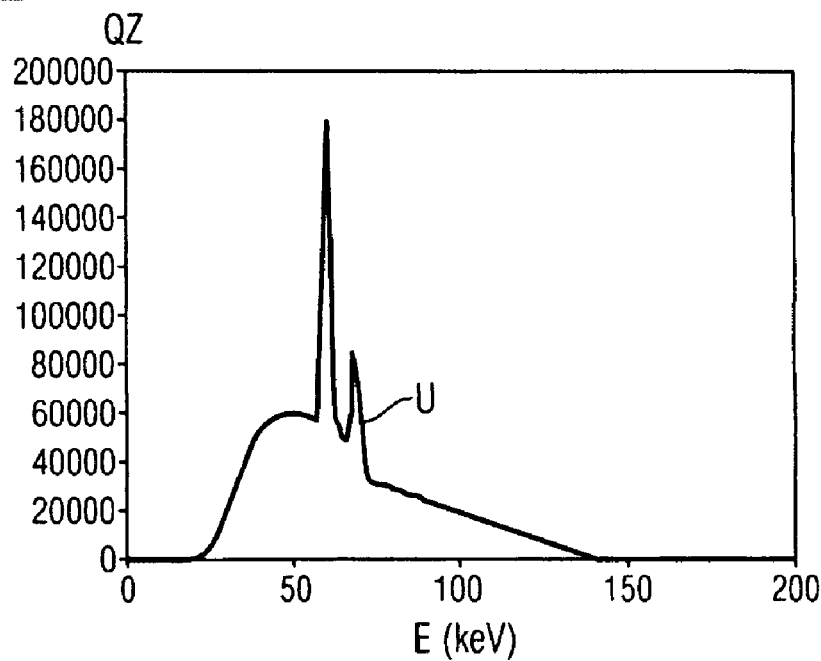
FIG. 12 shows a diagram of the X-ray spectrum of unfiltered X-ray radiation.
Figure 13:
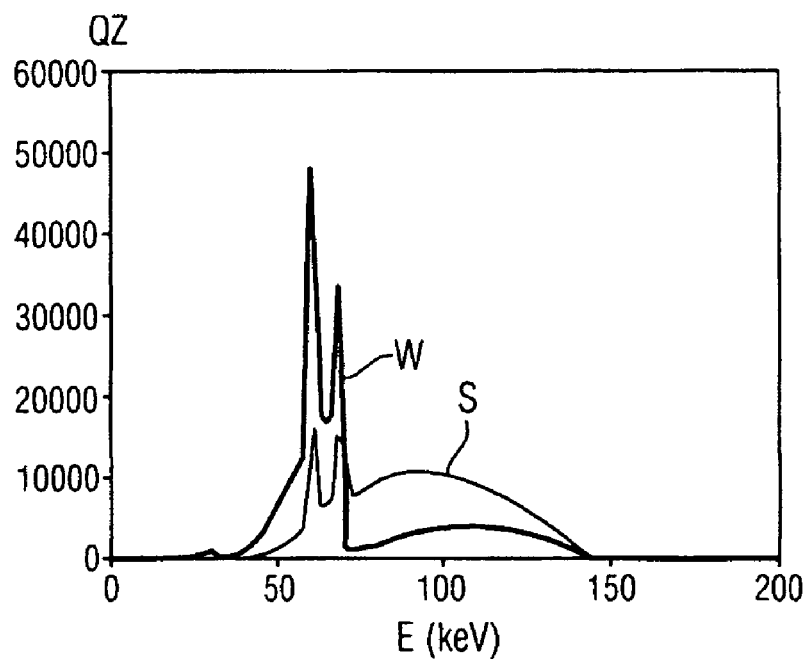
FIG. 13 shows a diagram of the X-ray spectrum of X-ray radiation filtered by two different filters.

The effect of the X-ray filter 16 on the spectrum of the X-ray radiation becomes apparent in FIGS. 12 and 13. FIG. 12 plots the number of quanta QZ over the energy distribution E for an unfiltered X-ray radiation up to 140 keV. Here, the peaks between 50 and 70 keV correspond to the characteristic X-ray radiation. FIG. 13 shows the X-ray spectra W and S after filtering the X-ray radiation using two different filters. Here, tungsten (curve W) and tin (curve S) are used as X-ray filter 16. It becomes apparent from this figure that the filtering basically effects attenuation and, in particular, a different distribution or profile of the X-ray spectrum. The filter material significantly attenuates the low-energy X-ray radiation, i.e. the X-ray radiation up to the maximum intensity $I_{max}$ of the unfiltered bremsstrahlung (the "bump" just before 50 keV in FIG. 12). This changed X-ray spectrum (W, S) is now used together with the unfiltered X-ray spectrum U in accordance with FIG. 12 for dual-energy evaluation.

The X-ray detector 8 is connected to an evaluation unit in a data-technical fashion; this evaluation unit is designed to separately evaluate the measurement signals from the two portions 8a, 8b and so the two data records obtained can be used in the reconstruction of dual-energy image data. On the one hand, the evaluation unit 18 is used for measurement data acquisition and, on the other hand, for reconstructing the image data. Further processing of the image data is performed on a workstation 19 which communicates with the evaluation unit 18. It is subsequently possible to proceed according to already known dual-energy processing methods using the reconstructed image data. This further processing generally occurs at an application level on the workstation 19.

FIGS. 3 and 4 illustrate a second embodiment variant of a computed tomography scanner 2, in which the X-ray filter 16 can be displaced in the Z-direction, i.e. transversely with respect to the X-ray detector 8. It becomes apparent from FIG. 4 that, in the Z-direction, the X-ray filter 16 is inserted so far into the beam fan 14 that it covers half of the beam fan 14, the filtered radiation component 14b being measured at the same time as the unfiltered radiation component 14a by the portions 8a, 8b of the X-ray detector 8.

A third embodiment variant of the computed tomography scanner 2 is illustrated in FIG. 5 to FIG. 11, in which the X-ray filter 16 can be rotated about a pivot point D lying on the central axis M of the beam fan 14.

The front view of FIG. 5 and the side view of FIG. 6 show a cover position of the X-ray filter 16, in which the complete beam fan 14 or the X-ray detector 16 is covered. The X-ray filter 16 is located in an upper region of the emitter diaphragm 6 and is aligned perpendicularly with respect to the central axis M and completely covers the beam fan. This position is referred to as the 12 o'clock position.

The 3 o'clock position according to FIG. 7 is reached when, starting from the position in FIG. 6, the X-ray filter 16 is rotated by 90° clockwise about the pivot point D; in this 3 o'clock position the X-ray filter 16 runs parallel to the central axis M and is arranged outside of the beam fan 14a and so it does not interfere with the latter. Hence, in this removed position, the beam fan 14a is completely uncovered and it is only the unfiltered X-ray radiation which is measured.

In the case of a further clockwise rotation of the X-ray filter 16, the 6 o'clock position is reached according to FIG. 8 and it likewise constitutes a cover position in which the X-ray filter 16 completely covers the beam fan 14, but, compared to the 12 o'clock position, said filter is located in the lower region of the emitter diaphragm 6.

Figure 9:
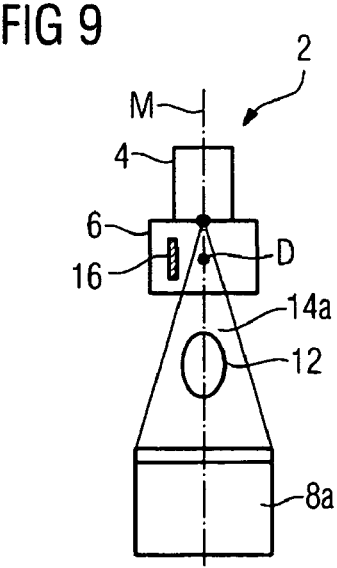

In the 9 o'clock position according to FIG. 9, the X-ray filter 16 is once again arranged parallel to the central axis M and so the beam fan 14a passes though the patient 12 in an unfiltered fashion. However, compared to the 3 o'clock position it is on the other side of the beam fan 14a.

Figure 10:
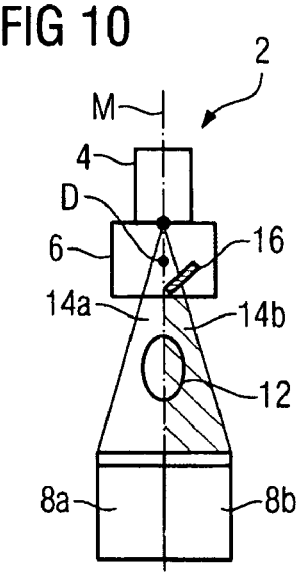
Figure 11:
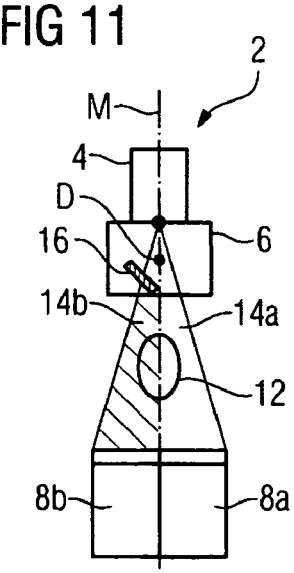

FIGS. 10 and 11 show two intermediate positions, namely a 5 o'clock position and a 7 o'clock position, in which the X-ray filter 16 extends obliquely with respect to the central axis M and only covers half of the beam fan 14.

In this third example embodiment, the position of the X-ray filter 16 is also always known with respect to the position of the X-ray detector 8 and so the size of the portions 8a, 8b is likewise known at all times during the rotation of the X-ray filter 16. The computed tomography scanner 2 is in particular designed for the X-ray filter 16 also performing a complete rotation about the pivot point D during a rotation of the X-ray emitter 4 about the axis A. It is also possible for the X-ray filter 16 to perform a number of, in particular whole, rotations about the pivot point D during one rotation of the X-ray emitter 4 about the patient 12. As a result of this method, a pulsing of the unfiltered and filtered X-ray radiation (14a, 14b) is obtained.

In all three illustrated example embodiments, the proportion of the unfiltered X-ray radiation 14a and the filtered radiation 14b is only half of what it is during normal operation of the computed tomography scanner 2 in accordance with FIG. 1 and FIG. 3 where no X-ray filter 16 is inserted. Therefore, double the number of rotations of the X-ray emitter 4 around the patient 12 are required in order to obtain a complete X-ray image for each radiation component 14a, 14b. Against this backdrop, a feed velocity of the patient couch 10 in the case of a spiral scan during the dual-energy operation of the computed tomography scanner 2 is only half the magnitude of the feed velocity during normal operation.

By using the X-ray filter 16, the computed tomography scanner 2 which only has one X-ray emitter 4 can be utilized for dual-energy imaging in a spiral scan. Complicated switching of the tube voltage in the X-ray emitter 4 is not required in this case. The operational principle described above can thus be realized particularly cost-effectively and in a technically simple fashion and so even conventional single source computed tomography scanners can additionally be operated as dual-energy scanners with little refitting expenditure.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computed tomography scanner for performing a spiral scan, comprising:
   a rotatable X-ray emitter for generating a beam fan;
   an X-ray detector, positioned diametrically opposite to said rotatable X-ray emitter;
   an evaluation unit; and
   an X-ray filter, arranged downstream of the rotatable X-ray emitter, a position of the X-ray filter being correlated to a position of the X-ray detector and said X-ray filter being partly inserted into the beam fan only during operation for generating an unfiltered radiation component and, simultaneously, a filtered radiation component of the beam fan, wherein the radiation components have different X-ray spectra and wherein the evaluation unit is designed for separate evaluation of a measurement signal of the unfiltered radiation component and a measurement signal of the filtered radiation component, to obtain dual-energy images, wherein the X-ray filter is displaceably arranged in the beam fan and the X-ray filter is arranged in rotatable fashion.

2. The computed tomography scanner as claimed in claim 1, wherein the position of the X-ray filter is correlated to that of the X-ray detector such that, during the evaluation, there is an assignment of the portions on the X-ray detector the two filtered and unfiltered radiation components are incident.

3. The computed tomography scanner as claimed in claim 2, wherein the X-ray filter is made of tin, aluminum, copper, titanium or tungsten.

4. The computed tomography scanner as claimed in claim 2, wherein the X-ray filter covers a portion of the X-ray detector in a defined direction of extent of the X-ray detector.

5. The computed tomography scanner as claimed in claim 4, wherein the X-ray filter covers half of the X-ray detector in the defined direction of extent.

6. The computed tomography scanner as claimed in claim 1, wherein the X-ray filter is made of tin, aluminum, copper, titanium or tungsten.

7. The computed tomography scanner as claimed in claim 1, wherein the X-ray filter covers a portion of the X-ray detector in a defined direction of extent of the X-ray detector.

8. The computed tomography scanner as claimed in claim 7, wherein the X-ray filter covers half of the X-ray detector in the defined direction of extent.

9. The computed tomography scanner as claimed in claim 1, wherein the X-ray filter includes a plurality of different X-ray filters, displaceable into the beam fan.

10. The computed tomography scanner as claimed in claim 1, wherein the X-ray emitter comprises an emitter diaphragm, and wherein the X-ray filter is installed in the emitter diaphragm.

11. The computed tomography scanner as claimed in claim 1, wherein the computed tomography scanner is operateable in normal operation without the X-ray filter and in a dual-energy mode with the X-ray filter, and wherein a feed velocity of a patient couch relative to the X-ray emitter is reduced in the dual-energy mode in the case of a spiral scan.

12. A computed tomography scanner, for performing a spiral scan, comprising:
   a rotatable X-ray emitter for generating a beam fan;
   an X-ray detector, positioned diametrically opposite to said rotatable X-ray emitter;
   an evaluation unit; and
   an X-ray filter, arranged downstream of the rotatable X-ray emitter, a position of the X-ray filter being correlated to a position of the X-ray detector and said X-ray filter being partly inserted into the beam fan only during operation for generating an unfiltered and, simultaneously, a filtered radiation component of the beam fan, wherein the radiation components have different X-ray spectra, the evaluation unit is designed for separate evaluation of a measurement signal of the unfiltered radiation component and a measurement signal of the filtered radiation component, to obtain dual-energy images, the X-ray filter is displaceably arranged in the beam fan and the X-ray filter is displaceably arranged such that during a complete rotation of the X-ray emitter, the X-ray filter is adjustable at least between a cover position in which the X-ray filter completely covers the beam fan and a removed position in which the X-ray filter completely uncovers the beam fan.

13. A method for controlling a computed tomography scanner for performing a spiral scan, wherein the computed tomography scanner comprises a rotatable X-ray emitter for generating a beam fan, an X-ray detector positioned diametrically opposite to the rotatable X-ray emitter, and an evaluation unit, the method comprising:
   arranging an X-ray filter downstream of the X-ray emitter, a position of the X-ray filter being correlated to that of the X-ray detector;
   forming an unfiltered radiation component of the beam fan and, simultaneously, a filtered radiation component of the beam fan using the X-ray filter, the X-ray filter being only partly inserted into the beam fan, wherein the unfiltered and filtered radiation components have different X-ray spectra; and
   evaluating a measurement signal of the unfiltered radiation component, separate from an evaluation of a measurement signal of the filtered radiation component, to obtain dual-energy images, wherein the X-ray filter is displaceably arranged in the beam fan and the X-ray filter is arranged in rotatable fashion.

* * * * *